(12) United States Patent
Havira et al.

(10) Patent No.: US 8,739,631 B2
(45) Date of Patent: Jun. 3, 2014

(54) SYSTEM AND METHOD FOR NON-DESTRUCTIVE TESTING OF RAILROAD RAILS USING ULTRASONIC APPARATUSES MOUNTED WITHIN FLUID-FILLED TIRES MAINTAINED AT CONSTANT TEMPERATURES

(75) Inventors: Robert Mark Havira, New Fairfield, CT (US); Anthony Iorfino, Bethel, CT (US)

(73) Assignee: Sperry Rail, Inc., Danbury, CT (US)

( * ) Notice: Subject to any disclaimer, the term of this patent is extended or adjusted under 35 U.S.C. 154(b) by 285 days.

(21) Appl. No.: 13/406,926

(22) Filed: Feb. 28, 2012

(65) Prior Publication Data

US 2013/0220019 A1   Aug. 29, 2013

(51) Int. Cl.
*G01N 29/24* (2006.01)
*G01N 29/04* (2006.01)

(52) U.S. Cl.
USPC .............. 73/636; 73/632; 73/635; 73/639

(58) Field of Classification Search
USPC ........... 73/624, 628, 632, 633, 635, 636, 637, 73/638, 639; 77/634
See application file for complete search history.

(56) References Cited

U.S. PATENT DOCUMENTS

| | | | |
|---|---|---|---|
| 4,165,648 A | | 8/1979 | Pagano |
| 4,174,636 A | * | 11/1979 | Pagano ........................... 73/636 |
| 4,302,976 A | * | 12/1981 | Bull ................................ 73/639 |
| 4,402,210 A | * | 9/1983 | Vandeberg ................... 73/12.09 |
| 4,700,574 A | | 10/1987 | Turbe |
| 5,161,413 A | | 11/1992 | Junker et al. |
| 5,578,758 A | | 11/1996 | Havira et al. |
| 5,780,744 A | * | 7/1998 | Hall et al. ........................ 73/597 |
| 6,055,862 A | | 5/2000 | Martens |
| 6,604,421 B1 | | 8/2003 | Li |
| 7,305,885 B2 | * | 12/2007 | Barshinger et al. ............. 73/602 |
| 7,849,748 B2 | | 12/2010 | Havira |
| 7,882,742 B1 | * | 2/2011 | Martens ........................... 73/636 |
| 2001/0032513 A1 | | 10/2001 | Havira et al. |
| 2006/0065055 A1 | * | 3/2006 | Barshinger et al. ............. 73/609 |

FOREIGN PATENT DOCUMENTS

WO   WO 2009-007817 A2   1/2009

OTHER PUBLICATIONS

International Search Report for PCT/US2013/027861 dated Jun. 24, 2013.

* cited by examiner

*Primary Examiner* — Helen Kwok
(74) *Attorney, Agent, or Firm* — McCormick, Paulding & Huber LLP (57) ABSTRACT

A rolling search unit including an ultrasonic device and a heat exchanger mounted within a fluid-filled tire may be utilized to perform ultrasonic testing on an underlying railroad rail. The ultrasonic device may transmit or receive ultrasonic beams into or from the railroad rail, and the heat exchanger may be utilized to maintain the temperature of the fluid within the tire at a preferred level or within a preferred range. In such a manner, the results of testing obtained using the rolling search unit may be standardized regardless of the ambient temperature in the environment where the testing is being performed, and regardless of any heat gained or lost by the rolling search unit during operation.

24 Claims, 8 Drawing Sheets

SYSTEM AND METHOD FOR NON-DESTRUCTIVE TESTING OF RAILROAD RAILS USING ULTRASONIC APPARATUSES MOUNTED WITHIN FLUID-FILLED TIRES MAINTAINED AT CONSTANT TEMPERATURES

BACKGROUND OF THE INVENTION

1. Field of the Invention

The present invention relates to improved systems and methods for performing non-destructive testing and analyses of railroad rails. More particularly, the present invention is directed to systems and methods for identifying flaws and defects in underlying railroad rails using ultrasonic detection means mounted within fluid-filled tires, wherein the fluid within the tires is maintained at a constant, desired temperature through the use of one or more heat exchangers.

2. Description of the Related Art

From time to time, and for various reasons, the rails of a railroad track may develop one or more detrimental flaws or defects. Such adverse conditions may include transverse defects, vertical shear or split-head defects, horizontal shear or split-head defects or the like that may originate from manufacturing and construction processes, environmental factors or wear-and-tear from normal use. These flaws or defects are typically observed in the head of a rail, but may also be found within the web and feet of the rail, around the peripheries of the bolt holes, or any other portion of the cross-section of the rail. Due to the nature of railway travel, in which locomotives weighing tens of thousands of pounds regularly carry hundreds of tons of freight over rails while traveling at varying speeds, cracks within the rails may expand or propagate throughout the rail heads over time. Such flaws or defects that are left unattended or unaddressed can lead to a variety of problems, the most serious of which may include catastrophic rail failures or train derailments, and may pose serious financial, health and safety risks to goods and personnel, as well as the railway industry as a whole.

Rail failures may be predicted and avoided through routine non-destructive inspection, which may enable railway operators to identify and cure hidden or infinitesimal flaws or defects within rails before they manifest into problems of much greater magnitudes. To detect such flaws or defects, vehicles or rail car-mounted apparatuses including ultrasonic inspection equipment have been built to travel along a railroad track, and to continuously perform ultrasonic testing of the underlying rails in situ by transmitting ultrasonic beams into the rails and analyzing any portions of the beams that may be reflected off flaws or defects.

One example of an ultrasonic railroad rail inspection system for in situ rail inspection including a wheel assembly having a fluid-filled tire for maintaining rolling contact with the head of an underlying rail is disclosed in U.S. Pat. No. 7,849,748 B2 to Havira. According to the teachings of Havira, the tire forms a contact patch with a head of an underlying rail and includes an ultrasonic transducer supported within the tire for projecting an ultrasonic beam along a beam axis through the fluid and the tire, and into the head of the underlying rail. The ultrasonic beam propagates through the underlying rail and is reflected by any defects or flaws that may be present therein, which may cause some or all of the beam signal to be returned to the transducer or received by another ultrasonic detector. The reflected portions of the signal are then analyzed by one or more computer processors to determine the type, magnitude or location of the flaw or defect from which the signal was reflected.

When an ultrasonic transducer is suspended within a fluid-filled tire, such as is disclosed in Havira, the tire and fluid provide the transmission medium between the ultrasonic transducer and the underlying rail. Due to the nature of sound travel, the strength and quality of the ultrasonic signals that are both delivered and received by the transducer depend upon the speed of sound in the fluid.

The speed of sound of longitudinal sound waves in a medium is generally dependent upon the medium's compressibility and density. In a liquid medium, the speed of sound is typically calculated according to the Newton-LaPlace formula shown in Equation (1), below:

$$c = \sqrt{\frac{K}{\rho}} \quad (1)$$

where c is the speed of sound in the medium; K is the bulk modulus of the medium, i.e., a measure of the medium's resistance to uniform compression; and ρ is the density of the medium.

Both the density and the bulk modulus (or compressibility) of a liquid are typically dependent upon the temperature of the liquid. In liquid water, the density varies widely within the range between the freezing and boiling temperatures of 0° C. and 100° C. (32° F. and 212° F.), respectively. For example, the density of water has been observed to follow a roughly parabolic plot between 0° and 100° C. (32° F. and 212° F.), with a peak density of approximately 1.0000 gram per milliliter (g/ml) at approximately 4° C. (39.2° F.), and with minimum densities of 0.9999 grams per milliliter (g/ml) at approximately 0° C. (32° F.), and 0.9581 grams per milliliter (g/ml) at approximately 100° C. (212° F.). Likewise, the bulk modulus of water also varies as a function of the temperature of the water, rising from a value of 293×10³ pounds per square inch (psi), or 2.02 gigapascals (GPa), at 0° C. (32° F.), to a peak of 334×10³ pounds per square inch (psi), or 2.30 gigapascals (GPa), at approximately 54.4° C. (130° F.), before descending to a value of 300×10³ pounds per square inch (psi), or 2.07 gigapascals (GPa), at 100° C. (212° F.).

Variations in the density and the bulk modulus of a liquid at various temperatures result in concomitant variations in the speed of sound throughout the liquid. For example, in *Speed of Sound in Pure Water*, 52 J. Acoust. Soc. of America 1442 (1972), Del Grosso and Mader developed a fifth-order polynomial equation for estimating the speed of sound within pure water as a function of temperature. Del Grosso and Mader identified a peak sound velocity in pure water of 1,555.147 meters per second (m/s) at 74.172° C. (165.51° F.), as well as speeds of 1,402.388 meters per second (m/s) at 0° C. (32° F.) and 1,543.109 meters per second (m/s) at 100° C. (212° F.). Therefore, according to Del Grosso and Mader, the speed of sound in liquid water may vary across the range of temperatures in the liquid phase by over ten percent.

Variations in the speed of sound in a liquid as a function of temperature are particular critical to the inspection and analysis of railroad rails using ultrasonic detection means mounted within fluid-filled tires. Because the liquid acts as the primary transmission medium between the transducer and the rail head, changes in the sound propagation and attenuation properties of the liquid may create widely varying ultrasonic inspection results, either within an individual analysis, such as when the temperature of the fluid within the tire heats up due to friction after many miles of travel, or between analyses, such as when tests are performed at different times of the year or at different ambient temperatures. Unless the variation in fluid temperature is accounted for, the results of ultrasonic inspections may not be standardized, and may prove unhelpful in identifying flaws or defects within the rail. In such instances, the diagnosis and correction of potentially catastrophic failures may be unnecessarily delayed or completely overlooked.

It is an object of the present invention to overcome one or more of the drawbacks and/or disadvantages of the prior art described above.

SUMMARY OF THE INVENTION

The present invention is directed to a system for detecting and inspecting certain types of defects in a rail, including a fluid-filled tire for maintaining rolling contact with a head of an underlying rail on which the carriage travels. The fluid-filled tire may include both an ultrasonic transducer and a heat exchanger mounted within the tire. The ultrasonic transducer may transmit ultrasonic beams through the fluid and the tire into the head of the underlying rail, while the heat exchanger may maintain the fluid within the tire at a predetermined or desired temperature.

In accordance with one aspect, the present invention is directed to an improved system for performing non-destructive testing of rails of a railroad track. The system may include at least one wheel assembly mounted to a probe carrier, suspended from a carriage, or provided by any other vehicle, wherein the at least one wheel assembly has at least one fluid-filled tire for maintaining rolling contact with an underlying rail. The system may further include a heat exchanger mounted within the tire, which may be a part of an independent, closed-loop fluid system that draws heat from, or introduces heat to, the fluid within the rolling tire by circulating a heat transfer medium therethrough. The system may further include sensors and/or control systems for monitoring either the temperature of the fluid within the rolling tire or the temperature of the heat transfer medium, and for providing heating or cooling to the heat exchanger, as necessary, in order to maintain the temperature of the fluid within the tire at or near a predetermined set point.

The systems and methods of the present invention may provide numerous advantages over the prior art. First, the systems and methods may ensure that inspection results are standardized across a single inspection by providing a single, constant fluid temperature despite any variations in temperatures throughout the inspection process or any heat that may be generated due to friction. Second, for the same reasons, the systems and methods may also standardize the results of periodic inspections performed throughout the year, i.e., in every season and at any temperature. Third, because the temperature of the fluid medium may be controlled or maintained at a desired level, the systems and methods enable testing to be performed at the most advantageous temperature for a particular fluid medium, i.e., at the temperature at which the acoustic properties of the fluid are maximized. Finally, the systems and methods enable the same rolling search unit to be utilized to conduct inspections and analyses in any location, regardless of the temperatures in the respective locations.

Other aspects and advantages of the systems and methods for performing non-destructive testing disclosed herein may be determined upon review of the Summary of the Invention, Figures, Detailed Description and Claims.

DESCRIPTION OF THE SEVERAL VIEWS OF THE INVENTION

DETAILED DESCRIPTION OF THE INVENTION

The present invention is directed to a rolling search unit including a fluid-filled tire for rolling along an underlying rail, wherein an ultrasonic transducer and a heat exchanger are mounted within the tire.

Figure 1:
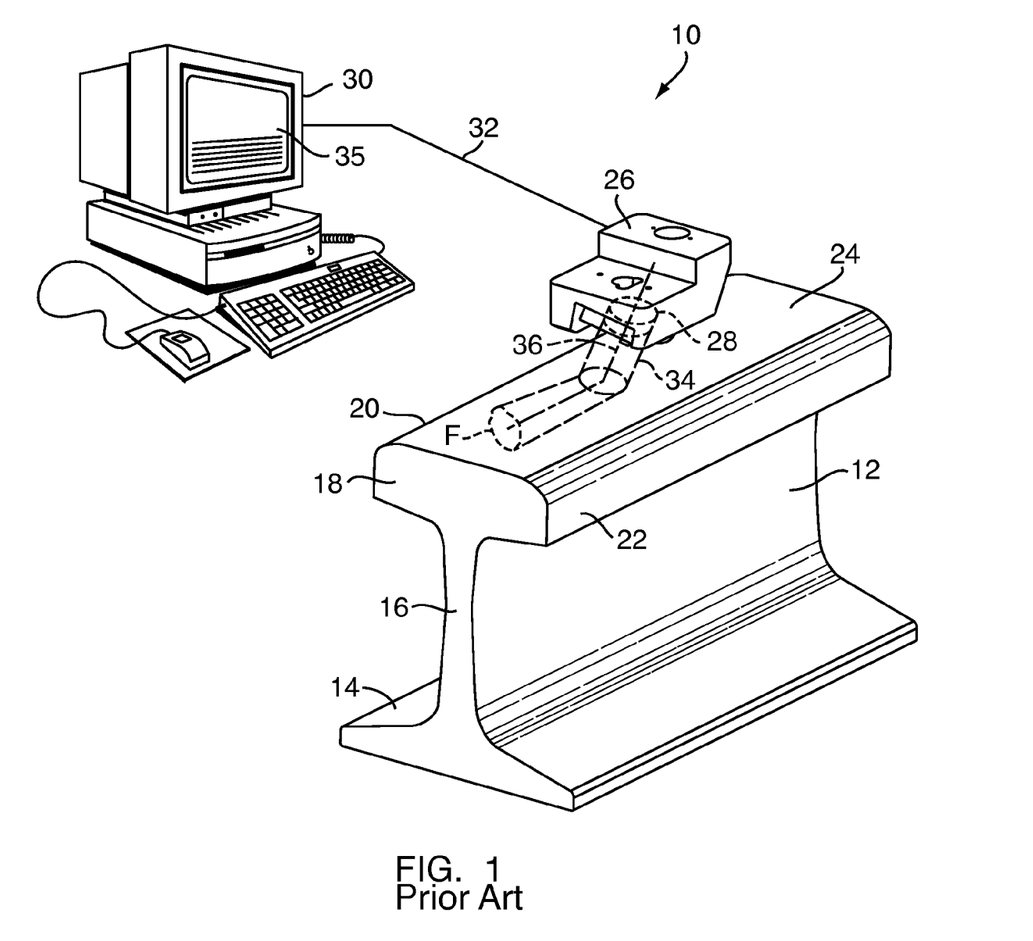
FIG. 1 is a schematic view of an ultrasonic railroad rail inspection system according to the prior art.

Various systems and methods for performing non-destructive testing of railroad rails using ultrasonic transducers are known to those of ordinary skill in the art, such as the systems and methods disclosed in U.S. Pat. No. 7,849,748 B2 to Havira. Referring to FIG. 1, an ultrasonic railroad rail inspection system 10 for inspecting a railroad rail 12 according to the prior art is shown. The rail 12 has a typical, known cross-sectional design with a base 14, a central web 16, and a head 18. The head 18 is shaped with a gauge side 20, a field side 22, and an upper running surface 24.

The system 10 further includes a flaw detector or sensor 26 containing one or more ultrasonic transducers 28, which are generally controlled by a central processing unit 30 of the computer 35, which is connected to the transducer by a cable 32. The ultrasonic transducers 28 are adapted to transmit and receive ultrasonic beams. When the central processing unit 30 sends a control signal to the transducer 28, the transducer 28 generates and transmits an ultrasonic beam 34 along a beam axis 36 toward the upper surface 24 of the rail 12. After a slight refraction, the beam 34 propagates through the head 18 until the beam 34 is reflected off of a flaw F embedded in the head 18. As is shown in the illustrated case in FIG. 1, some of the ultrasonic beam 34 is reflected back from the flaw F along the beam axis 36, and propagates through the head 18 of the rail 12, through the upper surface 24 of the rail 12 to the transducer 26 where the reflected beam is detected. The transducer 28 converts the reflected beam into a reflection signal that is sent to the central processing unit 30 through the cable 32. The central processing unit 30 analyzes the reflection signal in comparison to the transmitted signal, and identifies the existence, type, and location of the flaw F within the rail 12.

Figure 2:
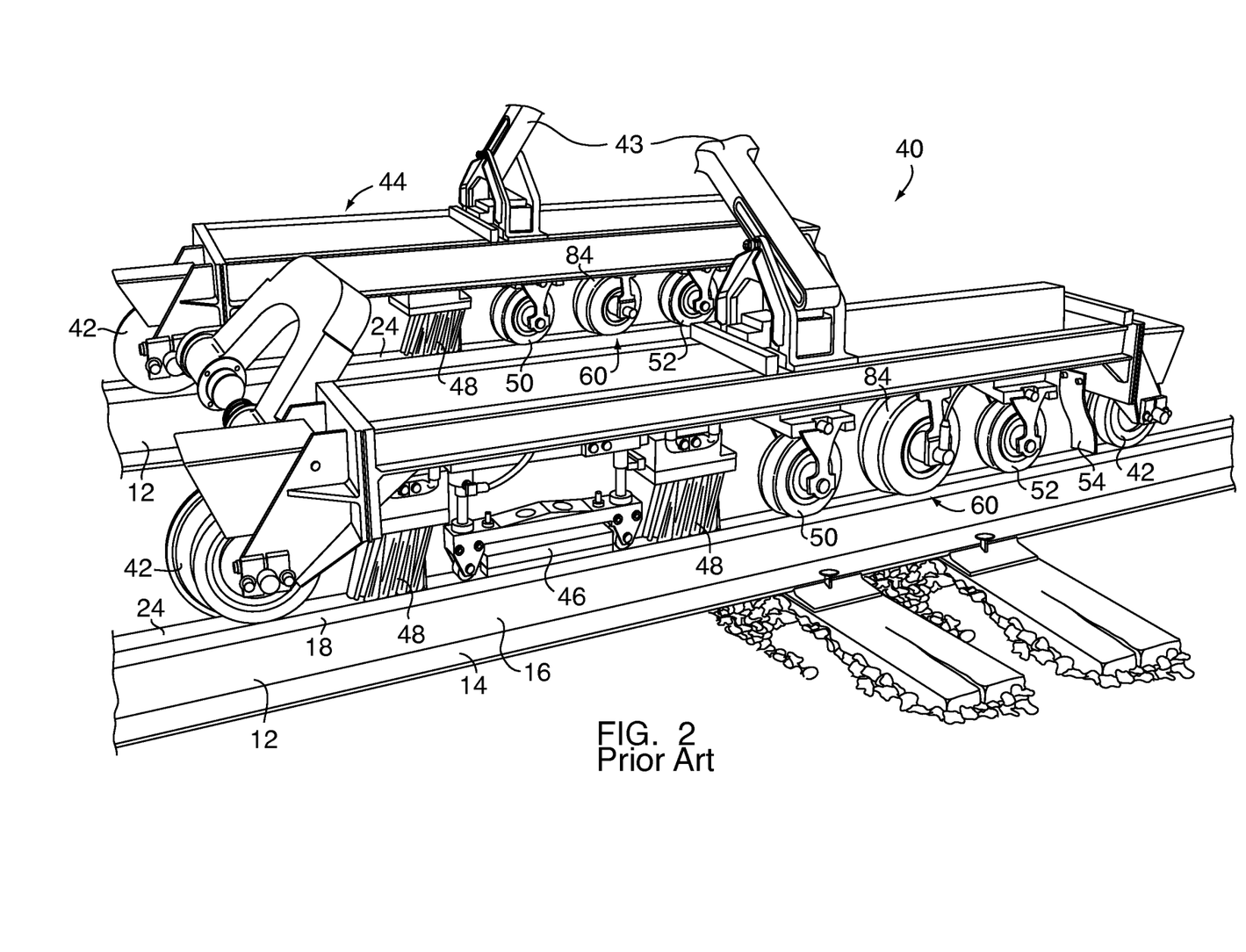
FIG. 2 is a perspective view of a carriage used in the rail inspection system of FIG. 1, according to the prior art.

Referring to FIG. 2, a carriage 40 or other probe carrier for performing an inspection operation is shown as suspended by links 43 under a rail car or inspection vehicle (not shown) that travels along rails 12 to perform in situ rail flaw detection and identification. The carriage 40 may include a set of four flanged carriage wheels 42 connected to the four corners respectively of a rectangular chassis 44 to guide the carriage 40 along the rails 12 in a substantially centered position when the carriage 40 is lowered onto the rails 12 to perform an inspection operation.

The carriage 40 may be equipped with any number of known railroad rail inspection devices and inspection accessories, such as an induction sensor assembly 46 and associated current induction brushes 48. The carriage 40 may also be equipped with one or more known ultrasonic rail inspection wheels 50, 52, 60 which utilize transducers set at various angles to detect flaws ahead of and behind the wheels relative to the direction of travel, as well as defects below the carriage 40 in the web of the rails 12. In addition, the carriage 40 may also be equipped with a plurality of rail cleaners 54 to remove debris from the rails 12 in advance of the sensors and flaw detectors. Any other form of probe carrier may be used to mount the rolling search units, and to perform an inspection operation, in accordance with the present invention.

Figure 3:
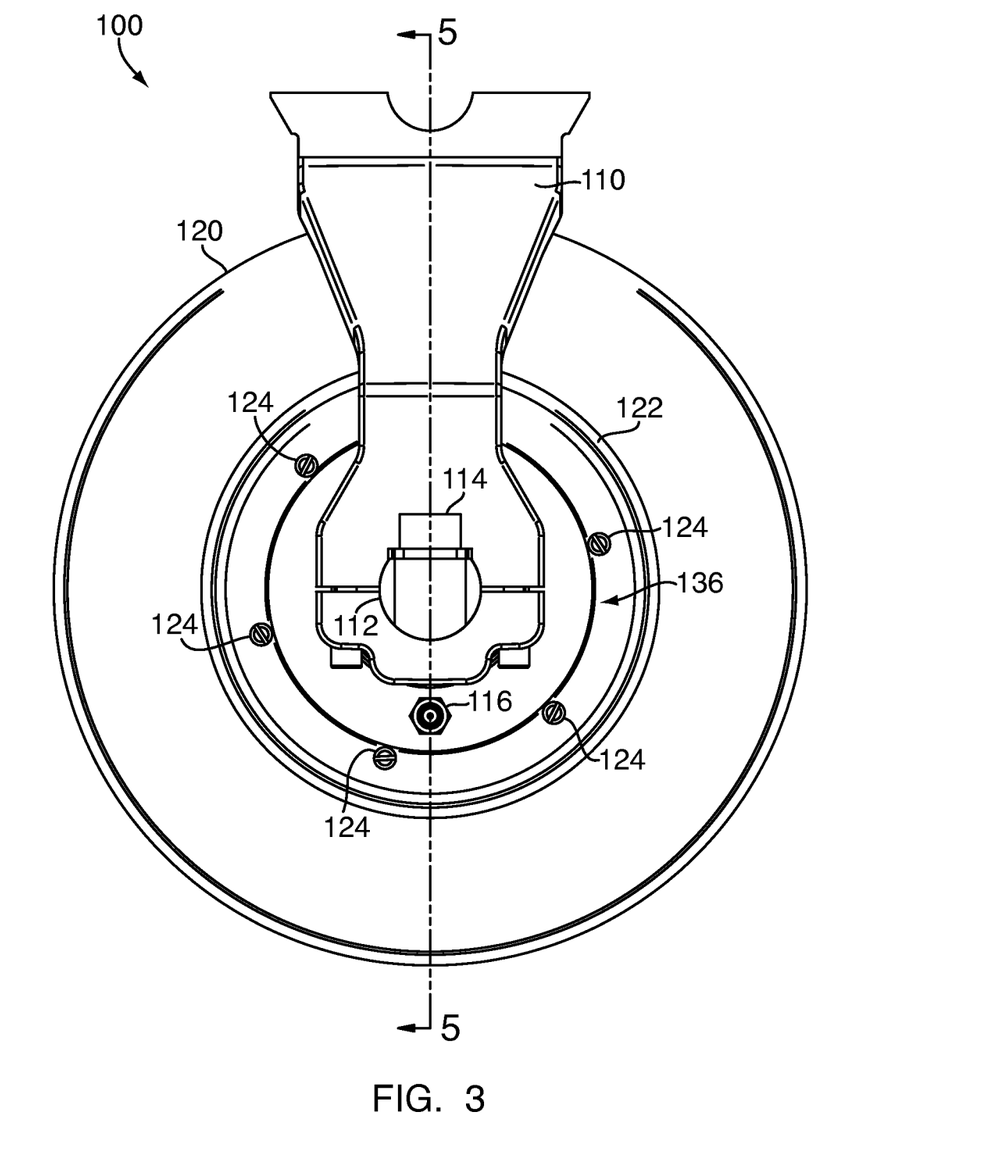
FIG. 3 is a side view of a rolling search unit according to one embodiment of the present invention.
Figure 4:
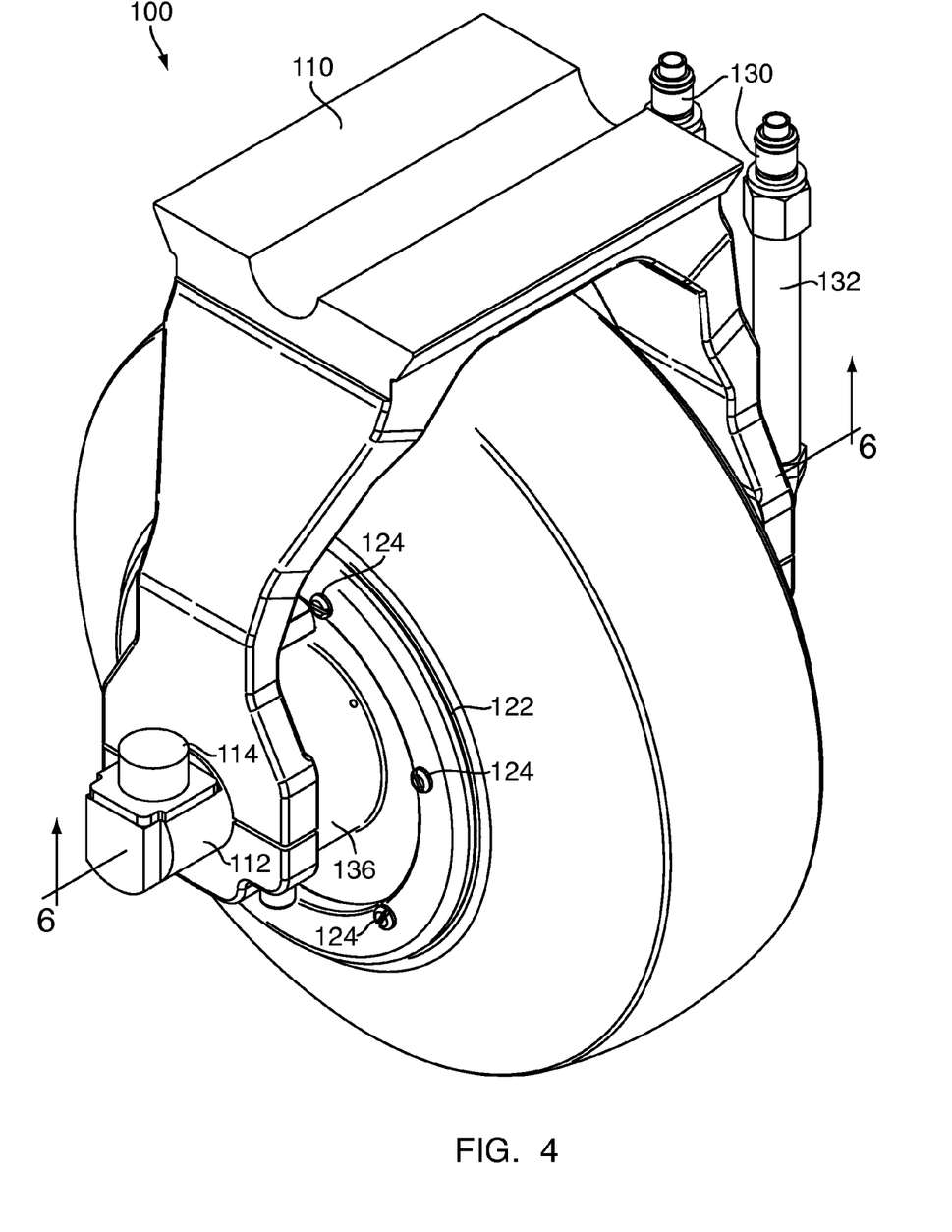
FIG. 4 is an isometric view of the rolling search unit of FIG. 3.

Referring to FIGS. 3 and 4, a rolling search unit 100 according to the present invention is shown. The rolling search unit 100 includes a bracket assembly 110, a shaft 112, a connector 114, a bleeder valve 116 and a tire 120 held between a clamping ring 122 and a wheel flange 136. The rolling search unit 100 may be linked with a heat transfer system (not shown) through connectors 130 and hoses 132, which provide a heat transfer medium to the rolling search unit 110 through supply and return headers.

The bracket assembly 110 is adapted to be mounted to the underside of a carriage or other vehicle capable of traveling on a railroad rail, and provides support for the shaft 112 and the tire 120. The connector 114 is mounted to an extension of the shaft 112 and is adapted to connect with a computer or other processing unit, such as the central processing unit 30 shown in FIG. 1. Preferably, the connector 114 is a multi-pin connector adapted to provide a versatile array of connections between the rolling search unit 110 and a computer or other processing unit.

Figure 5:
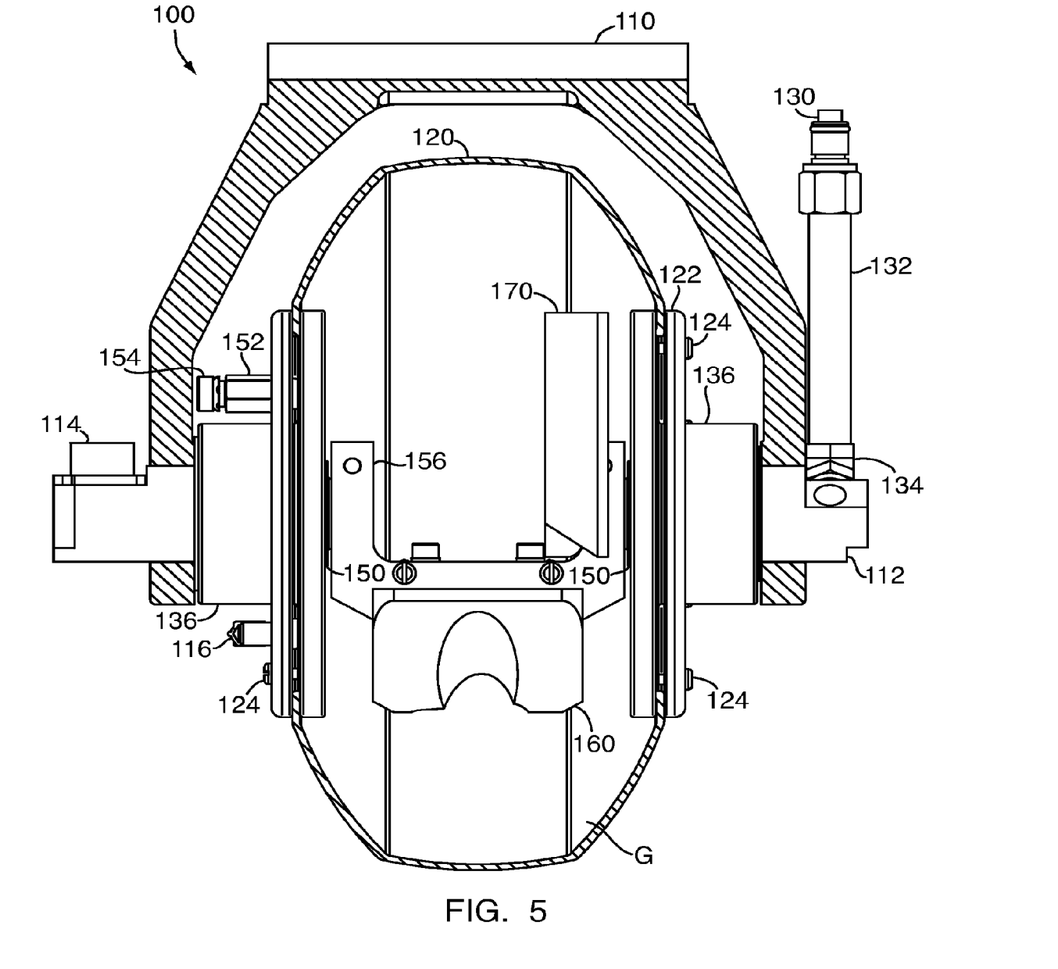
FIG. 5 is a cross-sectional view of the rolling search unit of FIG. 3, taken along the section lines 5-5.
Figure 6:
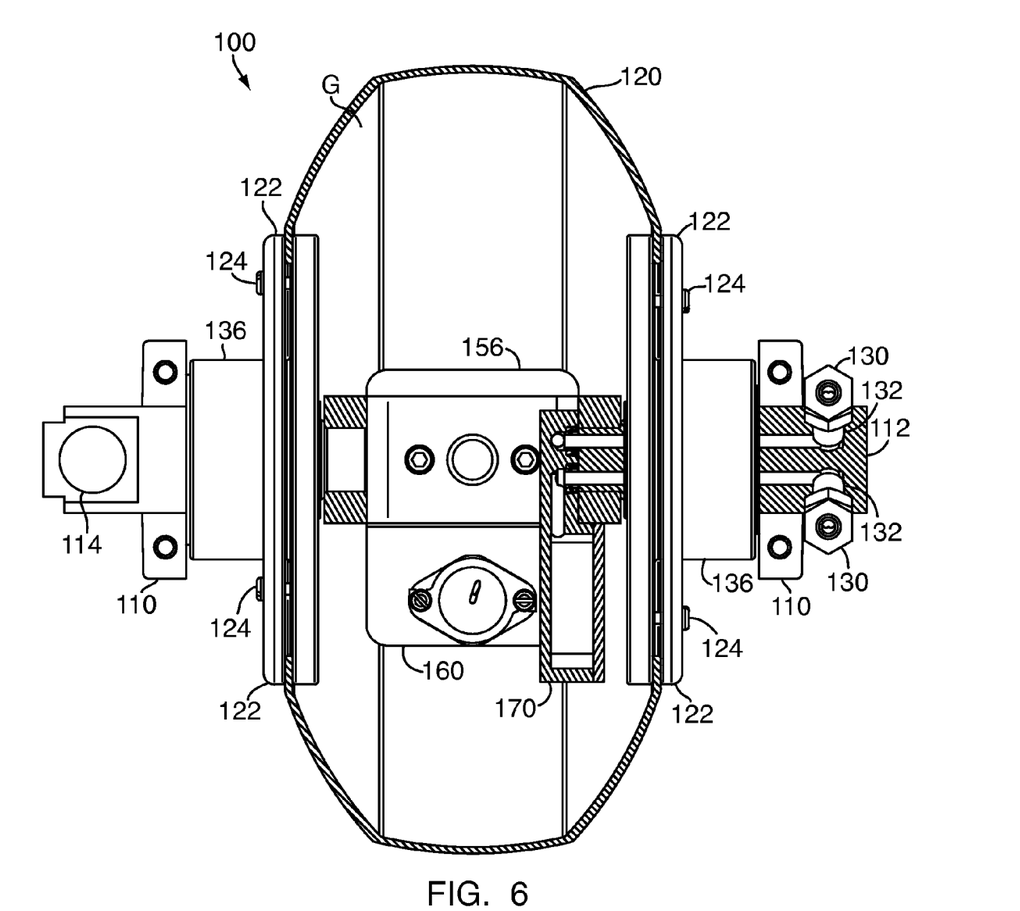
FIG. 6 is a cross-sectional view of the rolling search unit of FIG. 4, taken along the section lines 6-6.

Referring to FIGS. 5 and 6, cross-sectional views of the rolling search unit 100 of FIGS. 3 and 4 are shown. The rolling search unit 100 is shown as having an ultrasonic transducer 160 and a heat exchanger 170 supported within the tire 120, which is filled with fluid G.

The shaft 112 is shown as mounted to the bracket assembly 110 and providing support to the wheel flange 136. The shaft 112 may be formed from any material of sufficient strength, such as stainless steel. The tire 120 is clamped within clamping rings 122 through the use of fasteners 124, which fix and seal the internal perimeter of the tire 120. The clamping rings 122, tire 120, and wheel flanges 136 form a cavity that may be filled with a fluid. Preferably, the fasteners 124 are machine screws, although any form of fasteners may be used to fix the tire 120 within the clamping rings 122.

The tire 120 rotates freely in connection with the clamping rings 122 and wheel flange 136, and in contact with an underlying rail. In a currently preferred embodiment, the wheel flange 136 includes a bearing assembly positioned within retaining rings and held in place with a spring, to provide radial support for the shaft 112 and to reduce rotational friction.

The tire 120 is formed of a flexible material, such as polyurethane, and is filled with fluid G to a slight pressure, i.e., approximately 10 pounds per square inch (psi), or 68.950 kilopascals (kPa), gage. The tire 120 may be filled with fluid G prior to an inspection operation through filler valve 152, shown covered by stem bumper 154, or drained for servicing through bleeder valve 116, which is shown as covered by a cap. The rolling search unit 100 also includes seals 150 which prevent the pressurized fluid G from escaping the tire 120.

In a preferred embodiment, the fluid G within the tire is a mixture of water and ethylene glycol, although any suitable fluid may be used. Ethylene glycol is a preferred component of the fluid G because of its low freezing point, especially in mixtures with water. While pure ethylene glycol freezes at approximately −12° C. (+10° F.), a mixture of approximately fifty percent water and fifty percent ethylene glycol by volume freezes at approximately −35° C. (−31° F.).

Yoke assembly 156 is positioned within the tire 120. The yoke assembly 156 provides structural support within the tire 120 for ultrasonic transducer 160 and heat exchanger 170. The ultrasonic transducer 160 may be equipped to transmit ultrasonic beams through the fluid G and the tire 120, and into an underlying rail, and may further be equipped to receive beams reflected off flaws, defects or other features within the underlying rail.

The heat exchanger 170 is designed to transfer heat between the fluid G outside of the heat exchanger 170 within the tire 120, and a heat transfer medium passing internally through the heat exchanger 170, to an external heat transfer system. The heat exchanger 170 is connected to external supply and return headers through connectors 130, hoses 132 and elbows 134, which provide the heat transfer medium to the heat exchanger 170 through channels within the shaft 112. While heat exchangers according to the present invention may take any shape, the heat exchanger 170 shown in FIGS. 5 and 6 has an arcuate shape of a circular sector, and is sized to maximize the external surface area for heat transfer within the tire 120, and also to fit within the loaded free height of the tire 120. Additionally, while the heat exchanger 170 is shown in FIGS. 4-6 as having smooth, exterior surfaces, heat exchangers according to the present invention may have grooved or corrugated external surfaces in order to further enhance the transfer of heat, or have any other surface features as desired.

The heat exchanger 170 is designed to be a part of a closed-loop heat transfer system, which may include one or more heaters or chillers in fluid communication with the heat exchanger 170. Preferably, the heat exchanger 170 is designed to withstand internal operating pressures of approximately 60 pounds per square inch (psi), or 413.685 kilopascals (kPa), gage, and to maintain the heat transfer medium within the heat transfer system separate from the fluid G within the tire 120. Although the rolling search unit 100 is designed to maintain the fluid G and the heat transfer medium separate from one another, and to prevent the fluid G and the heat transfer medium from coming into direct contact with one another, the fluid G and the heat transfer medium are preferably the same fluid, i.e., a mixture of approximately fifty percent water and fifty percent ethylene glycol by weight. However, any suitable heat transfer medium may be utilized within a heat exchanger mounted inside a tire according to the present invention.

The connections 130 enable the rolling search unit 100 to be linked to a heat transfer system that may be maintained onboard a rail car, carriage or other inspection vehicle, and may include one or more heaters or chillers as well as temperature control equipment. Preferably, the connectors 130 are quick-connect male brass fittings that enable a rolling search unit 100 to be mated with a heat transfer system in a modular format, although any form of connector may be utilized to connect the heat exchanger 170 with the supply and return headers of a heat transfer system. Additionally, the hoses 132 may be formed of any material, such as insulated or sheathed rubber, in order to minimize the transfer of heat to or from the heat transfer medium from the ambient environment, and to maintain the heat exchanger 170 in fluid communication with the heat transfer system despite the various vibrations and shocks associated with the travel of the rolling search unit 100 along railroad rails.

Figures 7A, 7B, 7C:
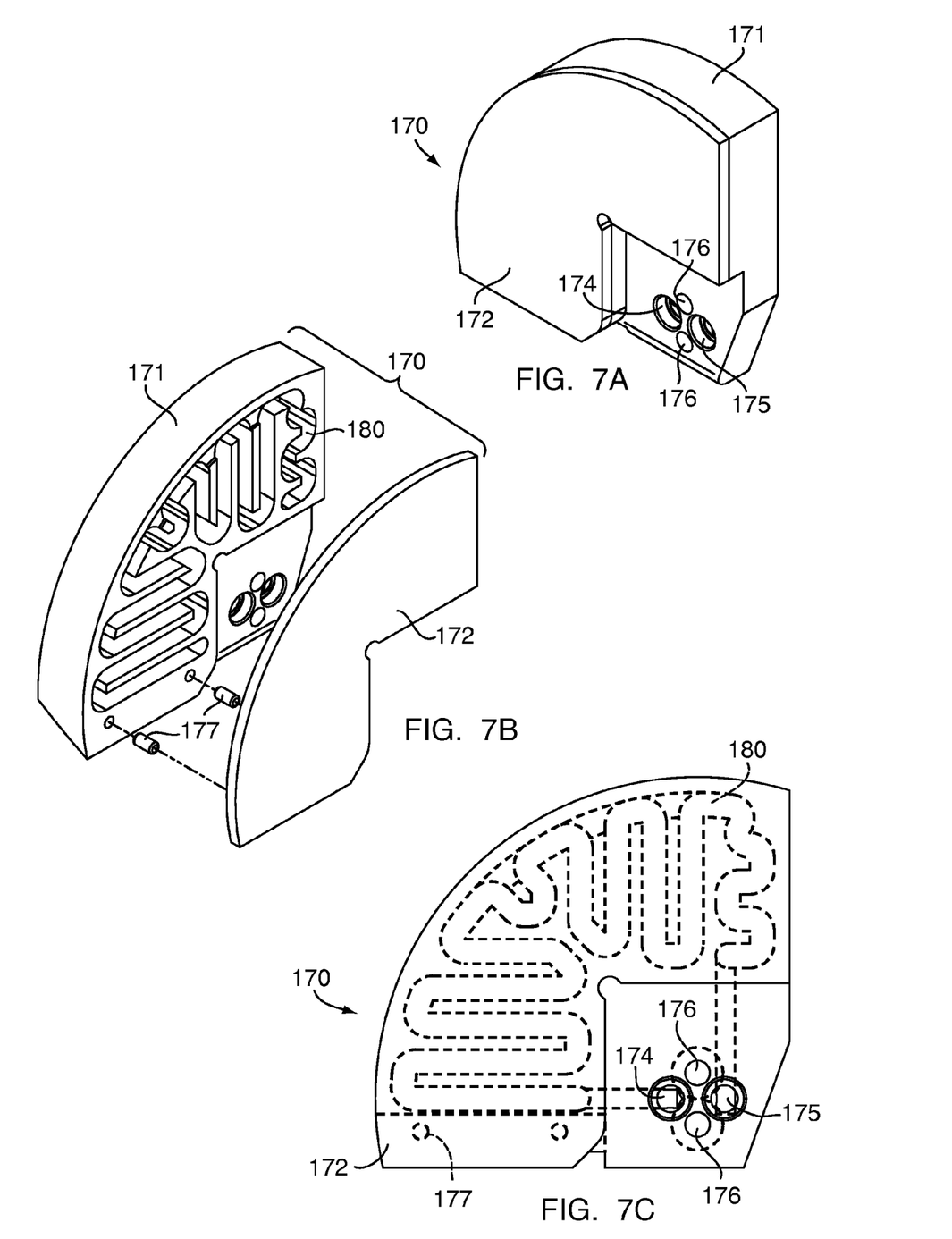
FIG. 7A is an isometric view of one embodiment of a heat exchanger for use in a rolling search unit according to one embodiment of the present invention.
FIG. 7B is an exploded isometric view of the heat exchanger of FIG. 7A.
FIG. 7C is an orthogonal view of one embodiment of a heat exchanger for use in a rolling search unit according to one embodiment of the present invention, showing an internal flow path for coolant flow in broken lines.

Referring to FIG. 7A, one embodiment of a heat exchanger 170 according to the present invention is shown. In FIG. 7A, the heat exchanger 170 is shown as including a base 171, a cover 172, an inlet 174, an outlet 175 and mounting holes 176. Referring to FIG. 7B, an exploded view of the heat exchanger 170 of FIG. 7A is shown, with the cover 172 removed from the base 171, exposing locating pins 177 and a flow path 180. Referring to FIG. 7C, the heat exchanger 170 of FIG. 7A is shown as an assembled unit, with the flow path 180 shown in broken lines.

The base 171 and the cover 172 form the exterior and interior surfaces of the heat exchanger 170, including the internal flow path 180. The inlet 174 and the outlet 175 are adapted to receive and discharge the heat transfer medium, respectively, from and to a heat transfer system. The mounting holes 176 may be used to mount the heat exchanger 170 within the tire 120, such as by bolts or other connection to the yoke assembly 156, as is shown in FIGS. 5 and 6.

Preferably, the heat exchanger 170 is a brazed plate device containing a lengthy, tortuous internal flow path 180 intended to maximize the length of flow of the heat transfer medium within the heat exchanger 170, and therefore to maximize the heat transfer between the fluid G and the heat transfer medium. The heat exchanger 170 may be formed from any desired materials, such as copper or brass. Additionally, although the heat exchanger 170 shown in FIGS. 7A, 7B and 7C includes a separate base and cover, heat exchangers according to the present invention may be formed as a single, integral unit, and need not include locating pins 177.

During operation, a rolling search unit 100 may be lowered into contact with a railroad rail to conduct an inspection, and a computer or other processing unit, such as the central processing unit 30 and computer 35 shown in FIG. 1, may deliver a signal to the ultrasonic transducer 160 to transmit one or more ultrasonic beams through the fluid G and the tire 120, and into the head of the underlying rail, as the unit 100 travels down the railroad track. Simultaneously, the temperature of the fluid G and/or the heat transfer medium leaving the heat exchanger may be monitored. If the temperature of the fluid G is too high or too low, the flow of heat transfer medium may be initiated, secured or controlled through the heat exchanger 170, until the desired temperature is reached. Heat may be generated within the tire 120 due to friction, such as bearing friction, friction generated by the rolling contact of the tire 120 with the underlying rail, and also friction caused by the sloshing of the fluid G within the tire 120.

The flow of heat transfer medium through the heat exchanger 170 may be controlled externally, based on the sensed temperatures of the fluid G or the heat transfer medium. The flow may be controlled by a computer or other processing unit, such as the central processing unit 30 and computer 35 shown in FIG. 1. Additionally, the flow may be controlled by the same computer or other processing unit that also controls the delivery of signals to the ultrasonic transducer 160, or by a separate system. Moreover, the flow of heat transfer medium through the heat exchanger may be initiated or secured, or increased or decreased, based on sensed or predicted factors. For example, the flow of heat transfer medium may be increased or decreased in anticipation of an increase or decrease in the speed of the rail car, to account for increased or decreased friction. Similarly, the flow of heat transfer medium may be increased or decreased due to changes in the ambient temperature in the environment, or based on a forecast of a temperature change in the ambient environment.

Figure 8:
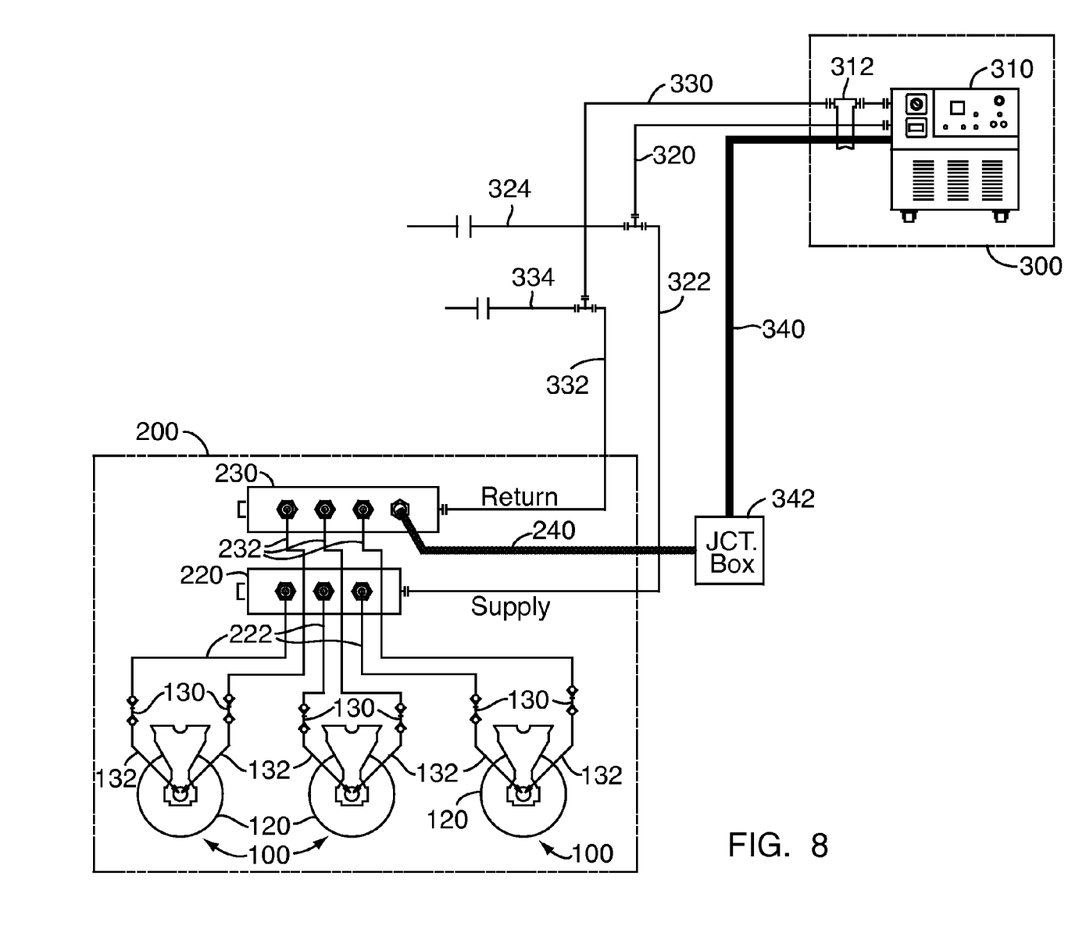
FIG. 8 is a piping diagram for a heat transfer system including a plurality of rolling search units according to one embodiment of the present invention.

Referring to FIG. 8, a piping diagram of one embodiment of a heat transfer system is shown. The system includes a carriage 200 mounted to an inspection vehicle 300, such as a rail car. Beneath the carriage 200, three rolling search units 100, such as the rolling search units shown in FIGS. 3-6 including tires 120, are installed and aligned for rolling contact with an underlying rail. The carriage 200 also includes a supply manifold 220 from which supply lines 222 extend to the rolling search units 100, and a return manifold 230 from which return lines 232 may extend from the rolling search units 100. Additionally, the return manifold 230 also has a sensing connection for a thermocouple 240, which monitors the temperature of the heat transfer medium within the return manifold 230. Alternatively, there may be one or more thermocouples for sensing temperatures of the fluid within the tire 120, temperatures of the heat transfer medium throughout the heat transfer system, or ambient temperatures.

The vehicle 300 includes a heat transfer apparatus 310, which may be a chiller, a heater, or another heat transfer device adapted to act as a chiller and a heater, as well as a filter 312. The heat transfer apparatus 310 provides a flow of a heat transfer medium at a desired temperature to supply line 320, which provides heat transfer medium to supply feed 322, and to the supply manifold 220 within the carriage 200. The heat transfer apparatus 310 receives a flow of heat transfer medium through discharge line 330, which receives heat transfer medium from the discharge manifold 230 through discharge feed 332. Although only one carriage 200 is shown in FIG. 8 as coupled with supply feed 322 and discharge feed 332, those of ordinary skill in the art will recognize that additional carriages may be provided with the heat transfer system. For example, a second carriage 200 may be coupled with supply feed 324 and discharge feed 334. Furthermore, although the carriage 200 shown in FIG. 8 includes three rolling search units 100, additional rolling search units may be added to the carriage 200 or other probe carrier according to the present invention.

The heat transfer apparatus 310 is functionally connected to a junction box 342 linked to the thermocouple 240, and receives signals regarding the temperature of the heat transfer medium within the return manifold 230. In the embodiment of the system shown in FIG. 8, the heat transfer apparatus may receive signals regarding the temperature of the fluid or the heat transfer medium, or other signals, and may increase or decrease the flow of the heat transfer medium, or may increase or decrease the temperature of the heat transfer medium, accordingly.

A heat transfer system, such as the system shown in FIG. 8, may be utilized to maintain the temperature of the fluid within a tire of a rolling search unit, such as the tire 120 of the rolling search units 100 shown in FIGS. 3-6, by controlling the flow rate and the temperature of the heat transfer medium passing through the heat exchangers mounted within the tires. For example, if the sensed temperature of the heat transfer medium within the return manifold 240 rises above or falls below a set point or beyond an acceptable range, the heat transfer system 310 may add heat to or remove heat from the heat transfer medium, or may increase or decrease the rate of flow of the heat transfer medium through the heat exchanger 170.

Systems and methods for performing rail inspections utilizing the rolling search units of the present invention provide a number of advantages over the prior art. First, by enabling operators to maintain the temperature of the fluid within the tires at constant levels, standardized test results may be obtained regardless of the temperature in the environment at the time of inspection. Second, the rolling search units of the present invention are versatile enough to be utilized in any location, from a hot, dry desert to a snowy, mountainous region, because the rolling search units will accommodate for differences in temperature and provide standardized test results accordingly. Third, the rolling search units of the present invention are also able to accommodate for heat generated through friction or from any other external source during operation. Fourth, because increases in temperature lead to increased pressures of the fluid within a tire, controlling the temperature of the fluid within the tire enables operators to minimize the maintenance and wear-and-tear of the tire or other components within the heat transfer system.

Moreover, as is set forth above, the systems and methods disclosed herein may be used in a variety of applications and are not limited to use in inspecting railroad rails. For instance, the systems and methods may be used to conduct ultrasonic inspections of any surface, such as roadways, foundations or other structures, or for any desired reason.

It should be understood that, unless otherwise explicitly or implicitly indicated herein, any of the features, characteristics, alternatives or modifications described regarding a particular embodiment herein may also be applied, used, or incorporated with any other embodiment described herein. Also, it should also be understood that the accompanying drawings are not drawn to scale.

Conditional language, such as, among others, "can," "could," "might," or "may," unless specifically stated otherwise, or otherwise understood within the context as used, is generally intended to convey that certain embodiments could include, but do not require, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

As may be recognized by those of ordinary skill in the pertinent art based on the teachings herein, numerous changes and modifications may be made to the above-described and other embodiments of the present invention without departing from the spirit of the invention as defined in the claims. Accordingly, this detailed description of currently preferred embodiments is to be taken in an illustrative, as opposed to a limiting sense.

Although the invention has been described and illustrated with respect to exemplary embodiments thereof, the foregoing and various other additions and omissions may be made therein and thereto without departing from the spirit and scope of the present disclosure.

What is claimed is:

1. A rolling search unit for performing an ultrasonic inspection of a railroad rail, comprising:
   a tire;
   at least one ultrasonic transducer suspended within the tire; and
   a heat exchanger suspended within the tire,
   wherein the tire is substantially filled with a liquid, and
   wherein the heat exchanger is adapted to receive a flow of a heat transfer medium from an external source for regulating a temperature of the liquid.

2. The rolling search unit of claim 1,
   wherein the heat exchanger comprises an inlet, an outlet, and an internal flow path between the inlet and the outlet.

3. The rolling search unit of claim 1,
   wherein the heat transfer medium comprises a mixture including at least one of water and ethylene glycol.

4. The rolling search unit of claim 1,
   wherein the liquid comprises a mixture including at least one of water and ethylene glycol.

5. The rolling search unit of claim 1, further comprising a temperature sensor for sensing a temperature of one of the liquid and the heat transfer medium.

6. An ultrasonic testing rail car comprising:
   a heat transfer apparatus;
   a probe carrier;
   at least one rolling search unit mounted to the probe carrier and comprising a tire substantially filled with a fluid;
   an ultrasonic device mounted within the tire and at least partially suspended in the fluid; and
   a heat exchanger mounted within the tire and at least partially suspended in the fluid,
   wherein the heat exchanger is in fluid communication with the heat transfer apparatus.

7. The rail car of claim 6, wherein the rail car is adapted to circulate a heat transfer medium between the heat transfer apparatus and the heat exchanger.

8. The rail car of claim 7, wherein the heat transfer apparatus is adapted to control a flow rate of the heat transfer medium between the heat transfer apparatus and the heat exchanger.

9. The rail car of claim 7, wherein the heat transfer apparatus is adapted to control a temperature of the heat transfer medium leaving the heat transfer apparatus.

10. The rail car of claim 6, wherein the ultrasonic device is adapted to transmit or receive ultrasonic signals.

11. A method for performing ultrasonic testing and inspection, the method comprising:
    providing an ultrasonic transducer within a tire filled with a fluid;
    placing the tire in rolling contact with a railroad rail;
    directing an ultrasonic beam from the ultrasonic transducer into the railroad rail; and
    maintaining the fluid at a predetermined temperature.

12. The method according to claim 11, the method further comprising:
    providing a heat exchanger within the tire.

13. The method according to claim 12, wherein the heat exchanger is in fluid communication with a heat transfer apparatus.

14. The method according to claim 13, wherein the heat transfer apparatus is adapted to circulate a heat transfer medium between the heat exchanger and the heat transfer apparatus.

15. The method according to claim 14, wherein the step of maintaining the fluid at the predetermined temperature comprises:
    sensing a temperature of the fluid.

16. The method according to claim 15, wherein the step of maintaining the fluid at the predetermined temperature comprises increasing or decreasing flow of the heat transfer medium if the temperature of the fluid rises above or falls below a predetermined set point.

17. The method according to claim 15, wherein the step of maintaining the fluid at the predetermined temperature comprises increasing or decreasing flow of the heat transfer medium if the temperature of the fluid is not within a predetermined range.

18. The method according to claim 15, wherein the step of maintaining the fluid at the predetermined temperature comprises increasing or decreasing a temperature of the heat transfer medium if the temperature of the fluid rises above or falls below a predetermined set point.

19. The method according to claim 15, wherein the step of maintaining the fluid at the predetermined temperature comprises increasing or decreasing a temperature of the heat transfer medium if the temperature of the fluid is not within a predetermined range.

20. The method according to claim 14, wherein the step of maintaining the fluid at the predetermined temperature comprises:

sensing a temperature of the heat transfer medium.

21. The method according to claim 20, wherein the step of maintaining the fluid at the predetermined temperature comprises increasing or decreasing a rate of flow of the heat transfer medium if the temperature of the heat transfer medium rises above or falls below a predetermined set point.

22. The method according to claim 20, wherein the step of maintaining the fluid at the predetermined temperature comprises increasing or decreasing a rate of flow of the heat transfer medium if the temperature of the heat transfer medium is not within a predetermined range.

23. The method according to claim 20, wherein the step of maintaining the fluid at the predetermined temperature comprises increasing or decreasing a temperature of the heat transfer medium if the temperature of the heat transfer medium rises above or falls below a predetermined set point.

24. The method according to claim 20, wherein the step of maintaining the fluid at the predetermined temperature comprises increasing or decreasing a temperature of the heat transfer medium if the temperature of the heat transfer medium is not within a predetermined range.

* * * * *